United States Patent [19]

Betush

[11] 4,375,963
[45] Mar. 8, 1983

[54] CONTROL UNIT FOR DENTAL HANDPIECES

[75] Inventor: Frank A. Betush, Carson, Calif.

[73] Assignee: Progressive Machine Products, Carson, Calif.

[21] Appl. No.: 277,116

[22] Filed: Jun. 25, 1981

[51] Int. Cl.³ .............................................. A61C 1/02
[52] U.S. Cl. ..................................................... 433/28
[58] Field of Search ..................... 433/28, 103, 77, 78; 251/9, 10

[56] References Cited

U.S. PATENT DOCUMENTS 3,986,262 10/1976 Casillas .................................. 433/28
4,117,861 10/1978 Betush .................................... 433/28

Primary Examiner—Robert Peshock
Attorney, Agent, or Firm—Keith D. Beecher

[57] ABSTRACT

A control unit is provided for supporting a multiplicity of dental handpieces of the high-pressure air-driven type, and which includes a plurality of holders for removably supporting the individual handpieces. Each of the holders is mounted on one end of a corresponding arm. The other end of the arm serves as a pinch block. Each arm is pivotally mounted on the frame of the control unit. An actuator is mounted on the frame of the control unit adjacent to each holder, and when a handpiece is inserted into the corresponding holder it engages the actuator and forces the corresponding arm to turn and to move, together with the holder and handpiece, to a down position. The other end of the arm then pinches one or more flexible tubes against a pinch bar in the control unit when the holder is forced to its down position. This action serves to cut off the supply of high pressure air to the handpiece, so that the high pressure air flows to the selected handpiece to drive the handpiece only when the holder is in its up position. As will be described, the control unit may also be used to control the flow of water to the selected handpiece to be directed onto the tooth being treated for cooling purposes.

5 Claims, 5 Drawing Figures

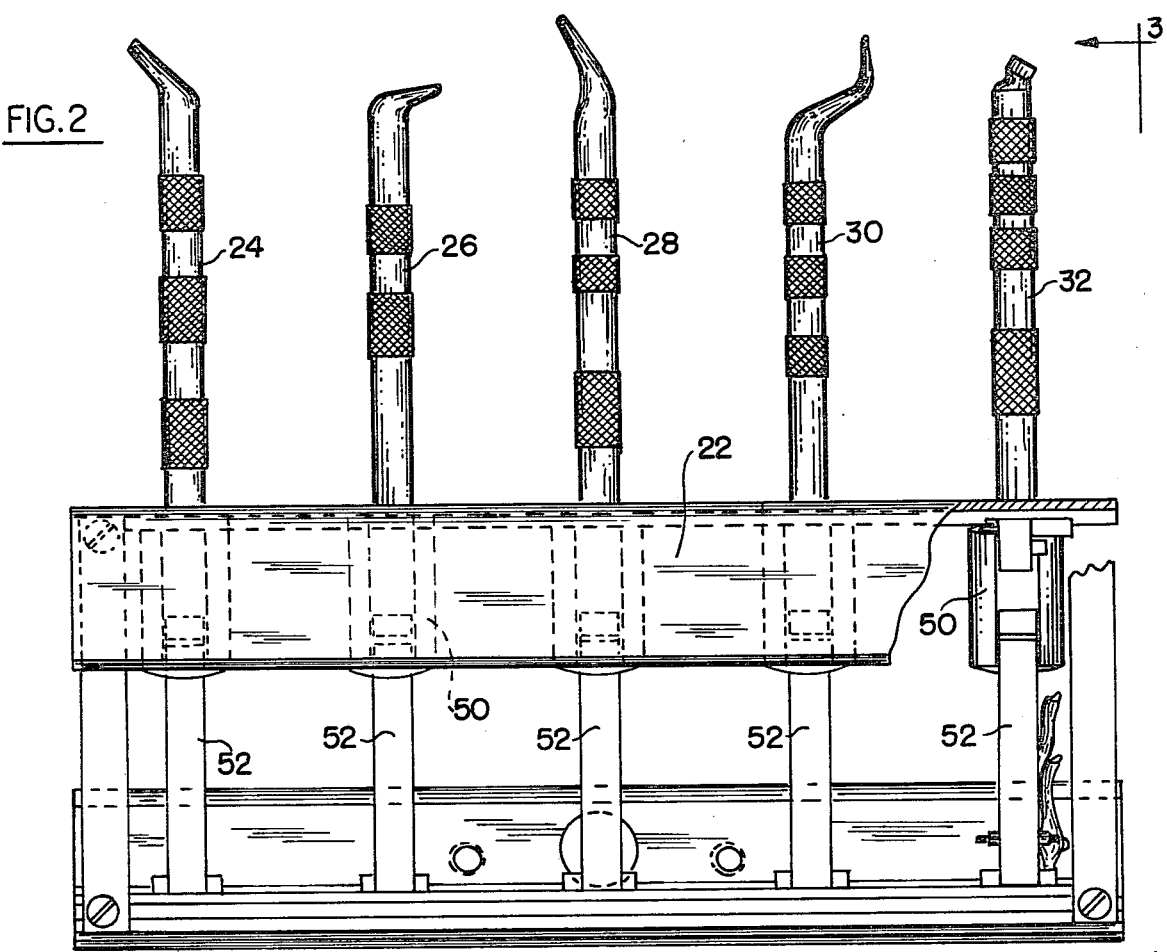
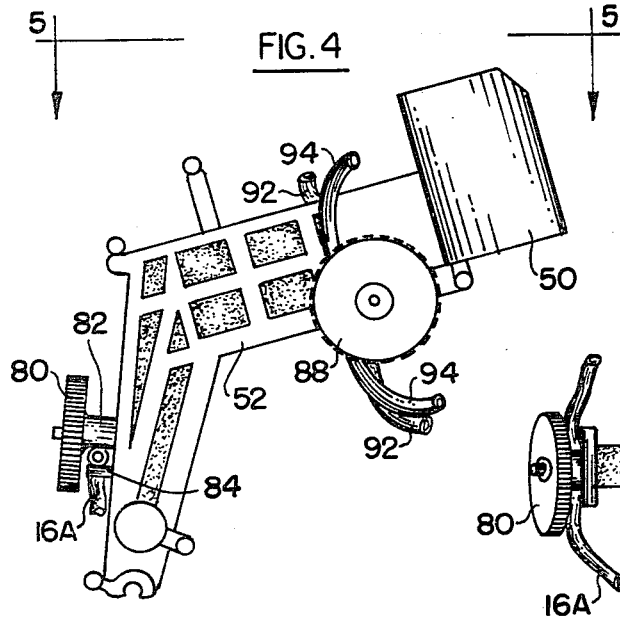
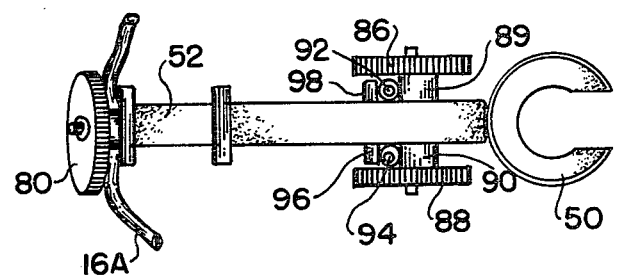

CONTROL UNIT FOR DENTAL HANDPIECES

BACKGROUND

U.S. Pat. No. 3,755,899, which issued to the present inventor, and which is assigned to the present assignee, discloses and claims a similar type of control unit. The control unit of the patent includes an over-center spring coupled to each of a number of pivotally mounted arms, with the hanpieces being respectively supported by the arms, and it requires that the arms themselves be flipped to the up positions after the handpieces have been removed to initiate the flow of air and/or water to the handpieces.

U.S. Pat. No. 4,117,861, which also issued to the present inventor, and which also is assigned to the present assignee, discloses a slightly different type of control unit in which the handpieces actuate corresponding pinch valve members directly as they are inserted into the holders. In the control unit of the present invention, like the control unit of the latter patent, positive valving action is obtained merely by inserting the handpiece into its holder, and by withdrawing the handpiece from the holder. This patent also discloses how pressure in a selected flow path may also inflate a "swell tube" which, in turn, operates other pinch valves.

As stated in the two patents referred to in the preceding paragraph, it is the usual practice in present-day dental offices to use a plurality of separate handpieces which are driven at high speeds by compressed air. In many instances, as mentioned above, the high speed handpieces also direct a stream of fluid, usually air or water, as a coolant into the drilled area of the tooth being treated.

It is also common practice in the prior art for each of the dental handpieces to be removably supported on individual holders which, in turn, are mounted on a console adjacent to the dental chair. Compressed air and pressurized water are supplied to the various handpieces in the prior art equipment through individual tubes. The air and water are obtained from the usual mains, and these fluids are usually supplied to the console through foot operated valves.

In the prior art, additional valves are provided in the console so that the flow of the pressurized air and water to the individual handpieces may be controlled. With such equipment, the dentist causes the air and water to be supplied to the console by actuating his foot operated valve, and he then causes air or water, or both, to be supplied to a selected handpiece, by actuating appropriate valves in the console.

However, the prior art console valving, in addition to being more expensive than the control unit of the invention, uses pistons with "O" ring or diaphragms and other such seals and actuators usually in complicated sequences of pilot operation to open a passageway to the selected handpiece. The present invention uses only simple mechanical linkage and direct action to pinch tubings, eliminating all such prior art complicated, costly valve blocks and passageways. The only fluid paths in this invention are the pinch tubes themselves, hence failures relating to sliding seals or diaphragms are eliminated in the illustrated form. Complete service and disassembly can be accomplished without tools due to the economical snap fit injection parts.

Although the controls illustrated are used for "high" pressure air, water, other liquids, gases, mixtures and slurries (carrying particulates) may be dispensed under positive or negative pressure in any pressure range consistent with available tubing technology for medical or industrial purposes. These fluids may begin to flow upon removal of the handpiece from the holder, or may be regulated by other interlock valves using pinch tubes or other valves, remotely controlled by foot actuators.

In the apparatus described in U.S. Pat. No. 3,755,899, each dental handpiece is supported in a holder on a pivotally mounted arm, and each arm includes a pinch block at one end which pinches a corresponding flexible tube to prevent the flow of fluid to the handpiece when the holder is in its down position, but which permits the flow of fluid through the tube to the selected handpiece when the holder is in its up position. Therefore, when the dentist selects a particular handpiece from the console, he flips the corresponding holder to its up position, and the handpiece immediately becomes activated, or is remotely activated by foot operated valves or regulators in series with the selected handpiece.

The control unit of the present invention, as described above, like the apparatus described in U.S. Pat. No. 4,117,861 achieves the desired valving effect merely by inserting the handpiece into or removing the handpiece from the corresponding holder. In the present control unit, such action causes the handpiece to engage the actuator so that the holder is firmly and positively moved to a down position in which the flexible tube or tubes are pinched; and then by removing the handpiece from the holder to cause the air and/or water flow path to be directed to the selected handpiece.

The control unit of the present invention, like the control unit of U.S. Pat. No. 4,117,861, is less complex than the prior art control units, as described above. Accordingly, it is relatively inexpensive in that it can be produced and sold at a fraction of the cost of the prior art consoles of the same general type. In addition, the control unit of the invention is easy and convenient to operate, and it does not require any action on the part of the dentist, except to remove a desired handpiece from its holder in the console.

BRIEF DESCRIPTION OF THE DRAWINGS

FIG. 2 is a top plan view of a control unit constructed in accordance with one embodiment of the invention;

FIGS. 4 and 5 are two views of an arm of the control unit with certain manual controls added to adjust the flow of fluid to the handpiece associated with that arm.

DETAILED DESCRIPTION OF THE ILLUSTRATED EMBODIMENT

Figure 1:
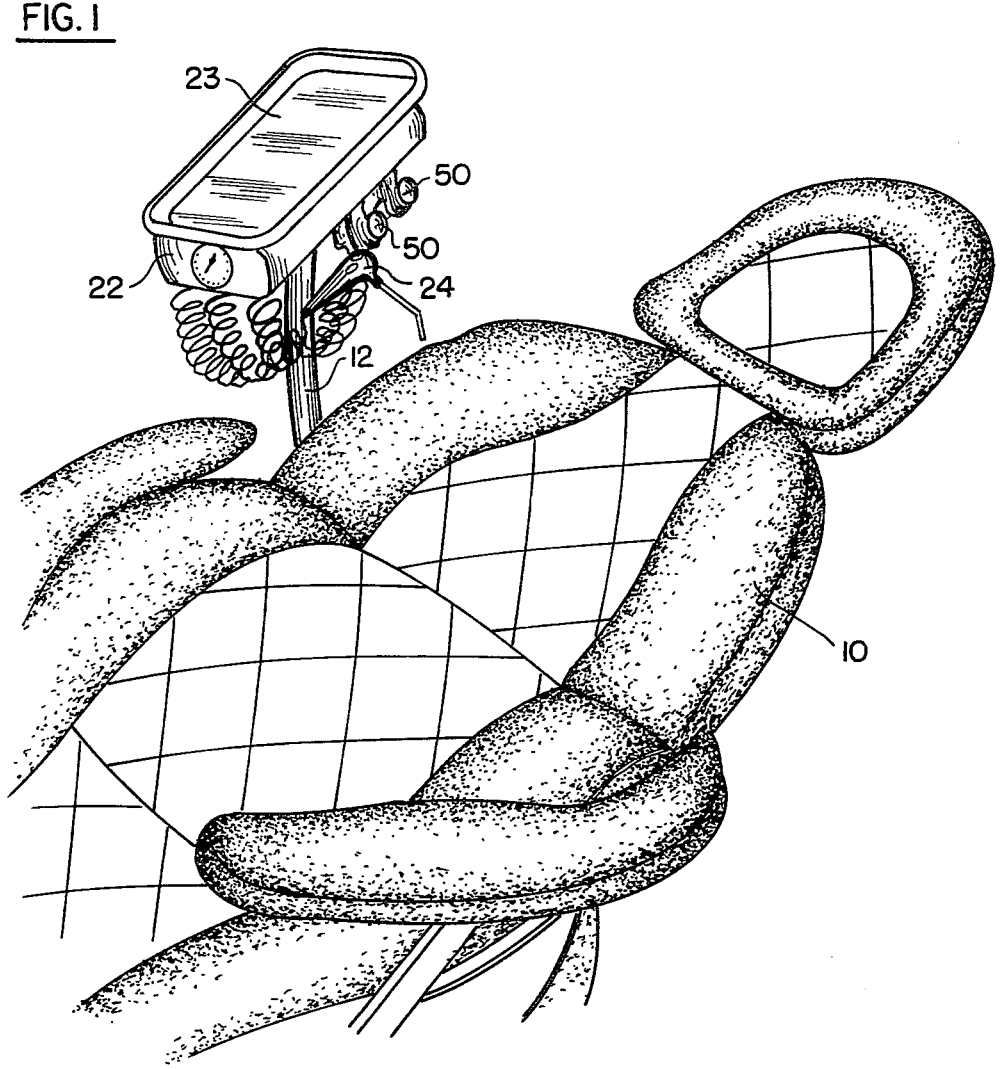
FIG. 1 is a perspective representation of a dental console which is constructed to incorporate a control unit embodying the concepts and features of the present invention.

As shown in FIG. 1, a console incorporating the control unit 22 of the present invention is mounted on a dental chair 10 by an upright hollow tubular member 12. An air tube and a water tube extend up the hollow interior of the tubular member 12. These tubes are coupled to any appropriate sources of water and compressed air, and the pressurized flow of these fluids through the respective tubes is controlled by the dentist by any appropriate means, such as by foot control valves. The tubes extend into control unit 22. A tray 23 may conveniently be mounted on the control unit.

The control unit 22, as shown in FIGS. 1 and 2, supports a plurality of dental handpieces 24, 26, 28 and 32 on a corresponding plurality of holders 50. These handpieces, for example, may be high speed compressed air driven drills, or other types, and which in some or in all instances emit a stream of water into the mouth of the patient. As will be described, the flow of air and/or water to a selected handpiece from the tubes 16 and 18 is controlled by the dentist, merely by removing the particular handpiece from its holder in the control unit and by replacing the handpiece in the holder.

Figure 3:
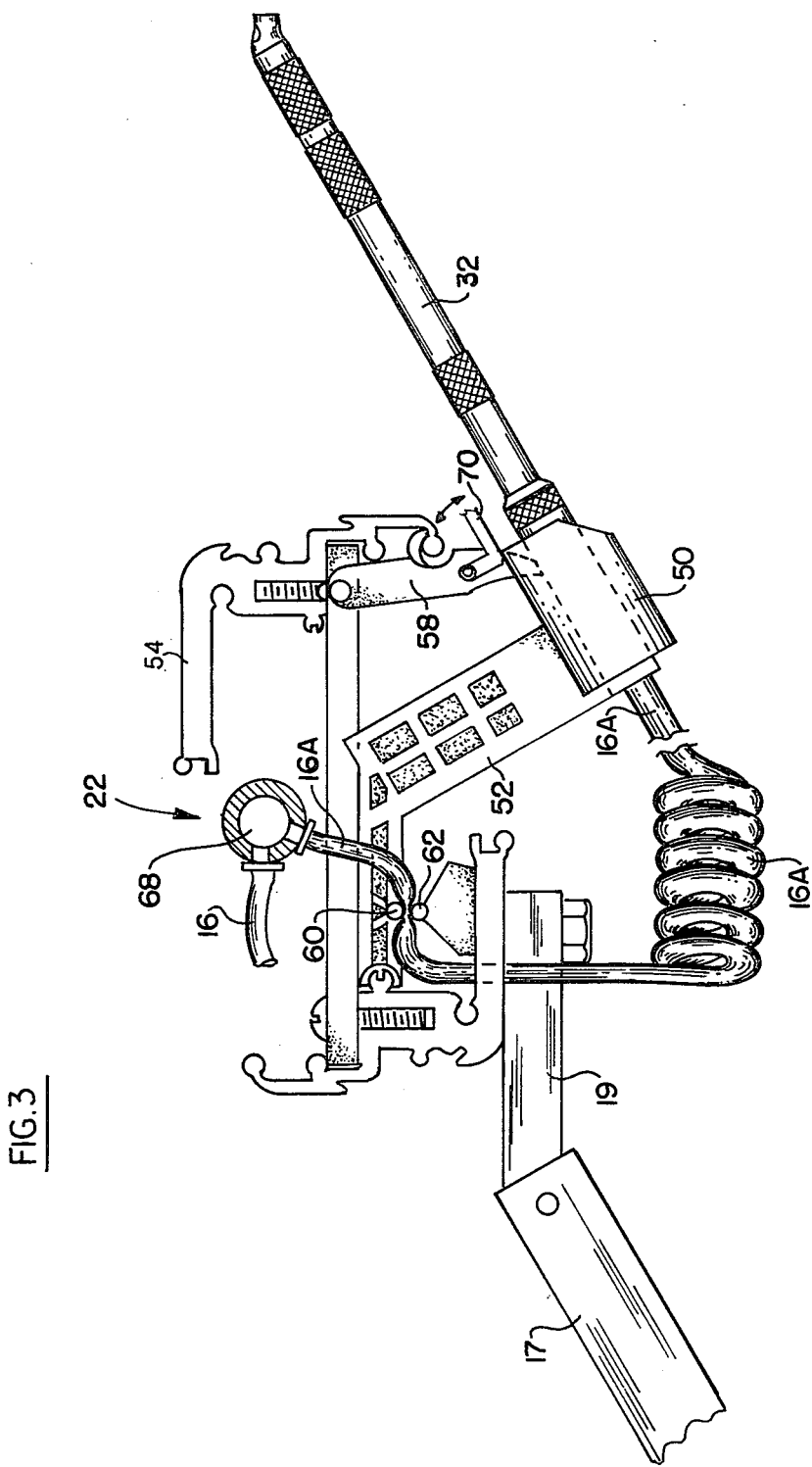
FIG. 3 is a side view of the control unit of FIG. 2, taken along the line 3—3 of FIG. 2.

The portion of the control unit associated with handpiece 32 is shown in detail in FIG. 3. It will be understood that similar structure in the control unit is associated with the other handpieces.

As shown in FIG. 3, handpiece 32 is removably held in holder 50 which, in turn, is mounted on the end of an arm 52. The arm 52 is pivotally mounted on the frame of the control unit 22 by a pivot assembly. The arm 52 is angularly movable in a counterclockwise direction by an amount limited by the frame. As the handpiece 32 is inserted in holder 50, it is engaged by an actuator 58 mounted on frame 54, so that the handpiece causes the arm 52 to move angularly in a clockwise direction causing tube 16A, for example, to be pinched between two pinch bars 60 and 62. Tube 16A is coupled to a manifold 68, to which the pressurized fluid from tube 16 is supplied for all the handpieces.

When the handpiece 32 is inserted in holder 50, the actuator 58 causes it to turn the holder in a clockwise direction, so that tube 16A is firmly pinched between the pinch bars 60 and 62, and the pressurized fluid is cut off. However, when the handpiece is removed from the holder 50, the resilience of the tube 16A causes the arm 52 to move a limited amount in the counterclockwise direction, and the fluid flows freely to the handpiece.

A locking lever 70 is pivotally mounted on actuator 58, and it may be turned to the position shown in FIG. 3 to engage holder 50, so that the handpiece 32 may be removed, if so desired, without releasing the pressurized fluid to the handpiece. Therefore, an assistant may service one instrument with its associated lock lever set to "off", while the operator uses another handpiece which is running.

As shown in FIGS. 4 and 5, a first manually turnable knob 80 is rotatably mounted on arm 52, and is keyed to an eccentric member 82. When the knob is turned, the eccentric member 82 squeezes the tube 16A, or other tube against a pinch bar 84, and the knob 80 may be turned to any angular position to establish a predetermined restriction in the tube 16A, so as to control the flow of the pressurized fluid to handpiece 32 when the handpiece is removed from the holder 50. A further pair of knobs 86 and 88 may be mounted on the arm 52, as shown in FIG. 5, which are respectively keyed to eccentrics 89 and 90, and these knobs may be independently turned to squeeze tubes 92 and 94 against corresponding pinch bars 96 and 98, so as to control the flow of pressurized fluid through the latter tubes. These knobs are conveniently placed so as to be accessible from the operator's work position.

The invention provides, therefore, an improved dental handpiece selector control unit which includes a plurality of holders which removably support the various dental handpieces, and which are mounted so that the flow of air and/or water to any handpiece may be controlled merely by removing the handpiece from its holder, and in which the flow is positively terminated merely by replacing the handpiece into its holder. As described, the handpiece selector control unit of the invention also includes manual controls for controlling the amount of air or water flow to any of the handpieces.

The expensive and relatively complex selector valves of the prior art control units are eliminated in the unit of the invention, and the selective control of a predetermined flow of water and air under pressure to the selected handpiece is achieved automatically by pinching the flexible tubes carrying the respective fluids to the handpieces in the manner and mechanism described above.

It will be appreciated that although a particular embodiment of the invention has been shown and described, modifications may be made, and it is intended in the accompanying claims to cover all modifications which come within the spirit and scope of the invention.

What is claimed is:

1. A control unit for supporting at least one dental handpiece, and the like, and for controlling the distribution of pressurized fluid thereto, said control unit including; a frame; an arm pivotally mounted on said frame; a holder for a handpiece mounted at one end of said arm; a stationary actuator mounted on said frame adjacent to said holder to be engaged by said handpiece when said handpiece is inserted into said holder and to cause the handpiece angularly to move said arm and said holder to a down position; a flexible tube extending through said frame to said handpiece for supplying pressurized fluid to said handpiece and for normally holding said arm in an up position; and a pinch member mounted on said frame in position to pinch said flexible tube against the other end of said arm and prevent the flow of said fluid to said handpiece when said handpiece is inserted into said holder and is engaged by said actuator so that said arm is in said down position and the other end of said arm has been moved angularly against said pinch member, and automatically to release said flexible tube and enable said tube to bias said arm to its up position and permit the flow of said fluid to said handpiece when said handpiece is removed from said holder.

2. The control unit defined in claim 1, and which includes two of said flexible tubes extending to said handpiece, one for supplying pressurized air to said handpiece, and the other for supplying pressurized water thereto.

3. The control unit defined in claim 1, and which includes a plurality of said arms respectively supporting a plurality of said dental handpieces at the ends thereof.

4. The control unit defined in claim 1, and which includes a manually operated latch mounted on said frame for selectively engaging said holder for holding said holder and said pinch member in said down position when the handpiece is removed.

5. The control unit defined in claim 1, and which includes a manually operated pinch valve mounted on said arm and engaging said flexible tube to vary the supply of pressurized fluid to the handpiece.

* * * * *